(12) United States Patent
Fichera (10) Patent No.: US 7,150,375 B2
(45) Date of Patent: Dec. 19, 2006

(54) APPARATUS AND METHOD FOR STORING SLIDES IN AN ANGULAR ARRANGEMENT

(75) Inventor: Stephen L. Fichera, Salem, NH (US)

(73) Assignee: Cytyc Corporation, Marlborough, MA (US)

( * ) Notice: Subject to any disclaimer, the term of this patent is extended or adjusted under 35 U.S.C. 154(b) by 231 days.

(21) Appl. No.: 10/675,451

(22) Filed: Sep. 30, 2003

(65) Prior Publication Data

US 2005/0067431 A1    Mar. 31, 2005

(51) Int. Cl.
*B65G 59/00* (2006.01)
(52) U.S. Cl. .......................... 221/67; 221/45; 221/124; 221/311; 312/50; 312/60
(58) Field of Classification Search ................ 221/311, 221/45, 123, 124, 67; 312/60, 50
See application file for complete search history.

(56) References Cited

U.S. PATENT DOCUMENTS

| 1,010,468 A | * | 12/1911 | Weaver | 312/61 |
| 1,576,010 A | * | 3/1926 | Swartz | 221/281 |
| 2,854,169 A | * | 9/1958 | Goodman | 221/104 |

* cited by examiner

*Primary Examiner*—Douglas Hess
(74) *Attorney, Agent, or Firm*—Vista IP Law Group LLP (57) ABSTRACT

An apparatus and method for storing slides in an angular, offset or fanning arrangement. The apparatus includes a base member and two support members. At least one of the base member, the first support member, and the second support member is arranged at an angle. With this configuration, the plurality of slides are angularly stacked on the base member and between the first and second support members. A bottom slide of the plurality of slides is dispensed through a slot defined between one of the lateral support members and the base member. The fanning arrangement can be a vertical fanning arrangement, a horizontal fanning arrangement, or a combination thereof.

22 Claims, 8 Drawing Sheets

APPARATUS AND METHOD FOR STORING SLIDES IN AN ANGULAR ARRANGEMENT

FIELD OF THE INVENTION

The present invention relates to slide storage mechanisms, and, more particularly, to an apparatus and method of storing slides in a non-overlapping arrangement, such as an angled, offset or fanning arrangement.

DESCRIPTION OF RELATED ART

Medical professionals and technicians utilize glass or plastic test slides to conduct various cytological testing and analyses. Slides are typically stored in and dispensed from a storage mechanism, such as a cartridge.

In some applications, a slide selection or transport system picks or selects a slide from the cartridge and carries the slide to a processing or analysis station. One known transport system includes a platform with fingers extending from the platform. When a slide is to be retrieved from the cartridge, the fingers are advanced to engage a side of a bottom slide in a stack of slides.

Conventional slide cartridges typically arrange slides in a stack in which one slide is placed directly on top of another slide. In other words, a bottom surface of a top slide rests directly on top of a top surface of an adjacent, lower slide, and the edges of the slide are aligned with each other. The transport system typically retrieves a slide at the bottom of the stack.

More specifically, the fingers include a section for carrying a slide and a lip that engages a side of the bottom slide. In use, the fingers are positioned so that the lip engages a side of the bottom slide, and the fingers are pushed forward so that the lip pushes the slide out from underneath the stack and onto the slide receiving section of the fingers.

Conventional slide storage and dispensing mechanisms, however, can be improved. For example, slide picking accuracy can be improved. In conventional transport systems, the fingers are typically required to select an individual slide, but may instead, inadvertently select two slides due to tolerances in stacking mating machined components, such as a cartridge base and fingers extending from the platform. More specifically, the platform fingers may not be able to engage only one slide at a time unless the engaging lip height is reduced, since the slides are aligned directly on top of each other. As a result of this lower lip height, conventional systems may not reliably and consistently select a single slide, thereby resulting in selection and processing errors and processing system adjustments and inefficiencies.

Further, stacking multiple slides on top of each other can result in substantial weight being applied to lower slides in the stack, particularly to the bottom slide. Excessive weight can also damage or break stacked slides. Additionally, it may be more difficult to remove a slide out from beneath the stack due to the downward forces as a result of excessive weight and lateral friction forces between the slides. Further, even assuming the slide is removed from the bottom of the stack, the weight and friction may result in the slide not being accurately placed on the fingers. While some lateral friction forces may be alleviated through the use of, for example, a spray lubricant, spraying individual slides is time consuming and inconvenient. These problems are amplified with larger stacks of slides, which are often utilized in larger systems and for efficient slide storage.

A need, therefore, exists for a slide storage apparatus and method of storing and dispensing slides in a more effective and reliable manner. Specifically, the slide storage mechanism and method should reduce the forces that are applied to lower or bottom slides, while permitting maximum engagement of slides so that individual slides can be reliably and consistently dispensed from the storage mechanism and onto platform fingers. The apparatus and method should also reduce damage to slides, improve slide selection accuracy, and improve slide processing.

SUMMARY OF THE INVENTION

In one embodiment, the present invention provides an apparatus, such as a cartridge, for storing a plurality of slides in an angular, offset or fanning arrangement. The apparatus includes a base member and two support members. One or more of the base member, the first support member, and the second support member is arranged at an angle relative to a horizontal or other reference. The plurality of slides are stacked in an angled, offset or fanning alignment on the base member and between the support members. A bottom slide of the plurality of slides is dispensed through a slot defined between a lateral support member and the base member.

Also in accordance with the present invention is an apparatus for storing a plurality of slides in an angular arrangement in which the base member has an angled top surface relative to a horizontal. First and second support members are substantially parallel to each other, and the plurality of slides are angularly stacked on the angled top surface and between the first and second support members. As a result, at least two bottom slides of the plurality of slides are offset from each other. A bottom slide is dispensed through a slot defined between a support member and the base member.

The angled top surface of the base member can be positioned at different angles depending on the desired fanning effect. The apparatus can also be tilted so that the plurality of angularly stacked slides are substantially parallel to the horizontal. Further, a lateral support members may support a portion of the weight of the plurality of slides in the tilted apparatus.

One or more additional slides may be stacked on top of the angularly stacked slides. The one or more additional slides may be stacked on top of each other. If necessary, a friction reducing member can be used to facilitate movement of the slide.

In yet further accordance with the present invention is an apparatus for storing a plurality of slides in an angular, offset or fanning arrangement that includes a first lateral support member arranged at a first angle relative to a horizontal and a second lateral support member arranged at a second angle relative to the horizontal. A base member is substantially parallel to the horizontal. The slides are angularly stacked on the base member and between the first and second support members so that at least two bottom slides of the plurality of slides are offset from each other.

In yet further accordance with the present invention is an apparatus for storing a plurality of slides in a fanning arrangement. A first lateral support member is positioned at a first angle relative to a horizontal, and a second lateral support member is positioned at a second angle relative to the horizontal. The first lateral support member and the second lateral support member are arranged at angles relative to the horizontal so that the plurality of slides are stacked on the base member in a fanning arrangement between the first and second support members.

The fanning arrangement can be a vertical fanning arrangement, a horizontal fanning arrangement, or a combination thereof. Further, in the fanning arrangement, slides that are positioned further away from the base member (on the higher slides) are arranged at a steeper angle relative to the horizontal compared to slides that are closer to the base member (the lower slides). The fanning arrangement can also create angled gaps and triangles between two adjacent slides.

BRIEF DESCRIPTION OF THE DRAWINGS

Referring now to the drawings in which like reference numbers represent corresponding parts throughout:

FIG. 1C is a side view of a typical finger of a slide transport system;

DETAILED DESCRIPTION OF PREFERRED EMBODIMENTS

In the following description, reference is made to the accompanying drawings which form a part hereof, and which show by way of illustration specific embodiments in which the invention may be practiced. It is to be understood that other embodiments may be utilized as structural changes may be made without departing from the scope of the present invention.

Figure 1A:
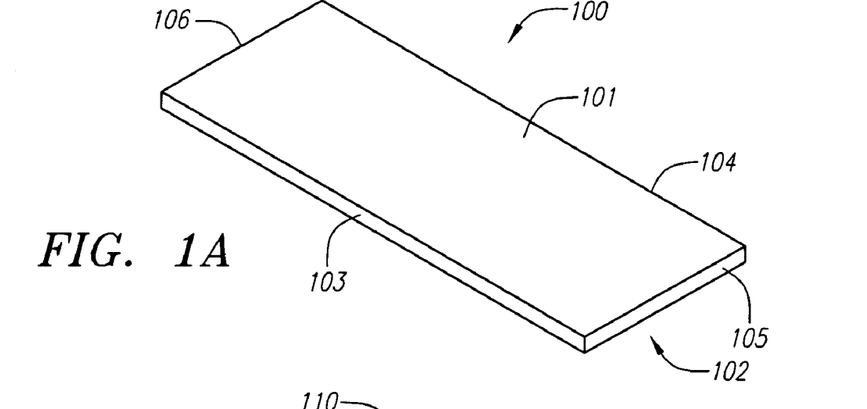
FIG. 1A is a perspective view of a typical sample or test slide, FIG. 1B generally illustrates a typical slide transport system.

Referring to FIG. 1A, a typical conventional test or sample slide 100 has a top surface 101, a bottom surface 102, a first side 103, a second or opposite side 104, a first edge 105, and a second or opposite edge 106. Persons of ordinary skill in the art will recognize that the present invention can be used with various slide 100 shapes and sizes.

Figures 1B, 1C:
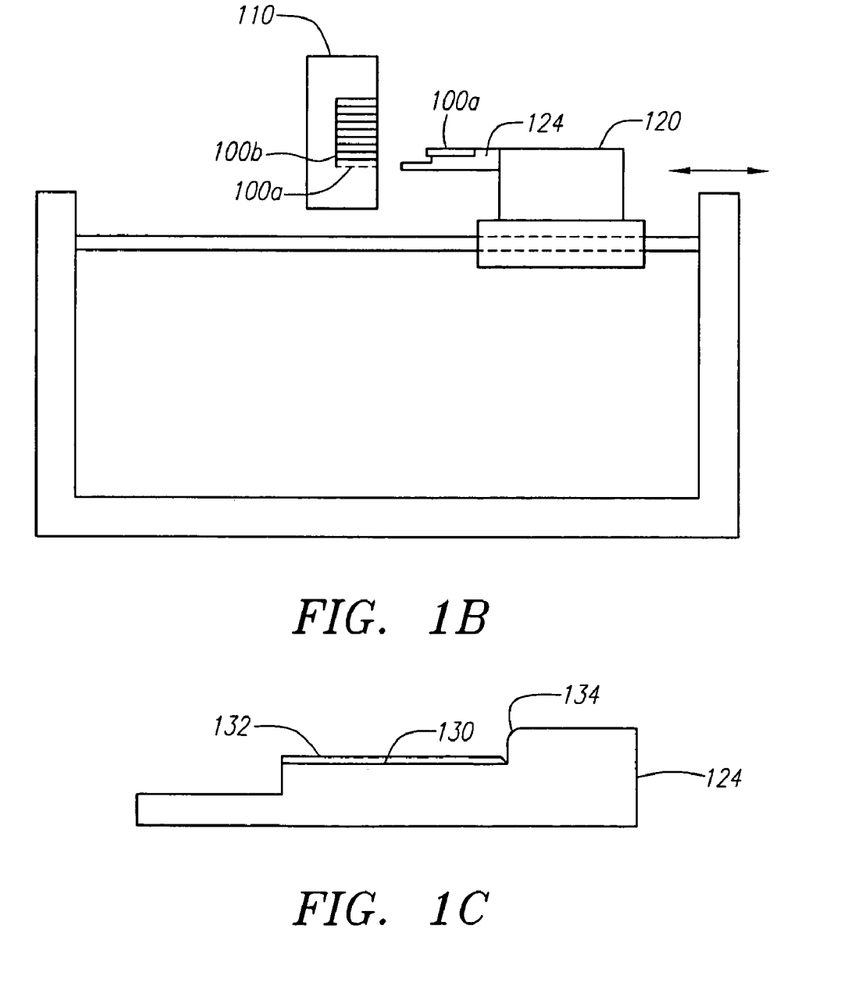

Referring to FIG. 1B, slides 100 are typically maintained in a storage apparatus or cartridge 110. A bottom slide 100a in a stack of slides 100 is typically removed or "picked" from the cartridge 110 by a slide selection or transport or translation system 120. A typical transport system 120 includes a platform 122 that is moved along or between various slide storage mechanisms 110 and processing devices or stations (not shown). Arms or fingers 124 extend from the platform 122. The fingers 124 engage/push the bottom slide 100 out from underneath the stack so that the slide 100a is placed on the fingers 124.

For example, referring to FIG. 1C, a typical finger 124 includes a slide area 130, a coating 132, such as a urethane coating, and an engagement lip 134. When the fingers 124 are positioned to receive the bottom slide 100a, the lip 134 pushes against a side of the bottom slide 100a so that the slide 10a is placed on the coated slide area 130. The coating 132 serves as a tacky or adhesive surface to prevent or reduce shifting of the slide 10a on the fingers 124. When the bottom slide 100a is pushed out from the stack and placed on the fingers 124, the slide 100a is carried to a processing device or analysis station by the transport system 120. The next slide 100b then moves into the "exit" position.

The present invention is directed to a slide storage apparatus or cartridge that arranges or stacks slides in a non-overlapping arrangement such as, for example, an angled arrangement, an offset or misaligned arrangement, and a fanning arrangement rather than typical conventional slide-on-slide, aligned or overlapping arrangements. The present invention reduces or distributes the weight and friction forces applied to slides, particularly the bottom slide in a stack, and allows for the maximum engagement of the exit slide so as to enable the transport system to reliably select individual slides.

In this specification, a "non-overlapping" or "offset" arrangement refers to an arrangement of slides in which the edges of one slide do not overlap or are not aligned with the edges of an adjacent slide, such as the next slide above or below the subject slide. Exemplary non-overlapping arrangements include angled or angular arrangements and fanning arrangements. An "angled" or "angular" arrangement includes slides that are arranged or rotated at an angle relative to a horizontal and one or more horizontal slides that are stacked at an angle. A "fanning" arrangement includes slides that are arranged in a vertical or horizontal fanning arrangement. For example, a fanning arrangement can include slides that are stacked so that the edges extend to different lengths. As a further example, the slides that are further away from the base member may be arranged at a steeper angle relative to the horizontal compared to slides that are closer to the base member, thereby generating an angled gap between two adjacent slides. Thus, a fanning arrangement may include slides arranged in angular and offset arrangements, and angularly arranged slides may include slides arranged in fanning and offset arrangements.

Figure 2A:
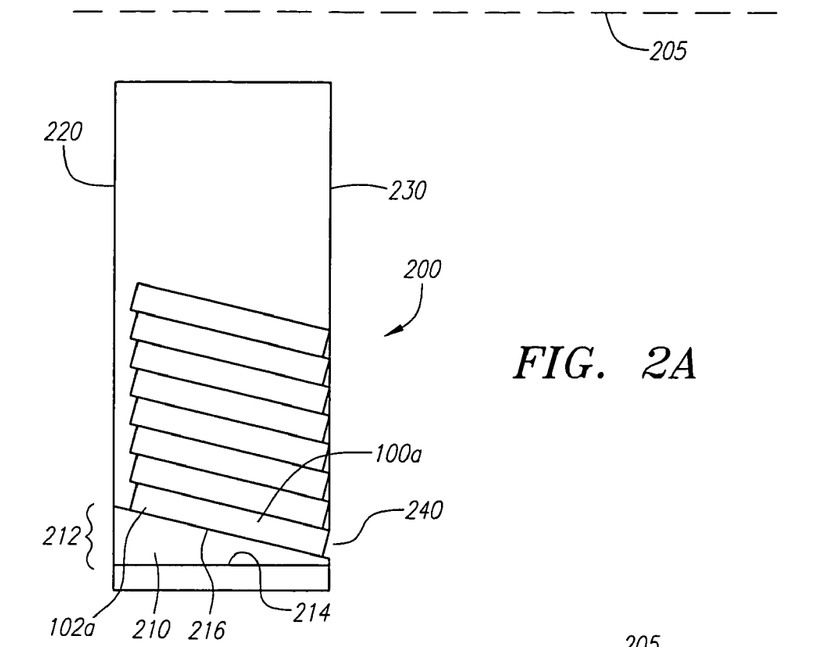
FIGS. 2A–B are a side views of one embodiment of the present invention that includes an angled base member.

Referring to FIG. 2A, in one embodiment of the present invention, a slide storage apparatus or cartridge 200 includes a base member 210, a first lateral support member 220, and a second lateral support member 230. Slides 100 can be dispensed from the cartridge 200 through a slot 240 defined between one of the lateral support members (e.g., the second internal support member 230) and the base member 210.

In a specific implementation, the angle 214 of the top surface 216 of the base member 210 relative to the horizontal 205 can be from about 8 degrees to about 12 degrees, preferably about 10 degrees. In the depicted embodiment, the lateral support members 220 and 230 are generally parallel to each other and perpendicular to the horizontal 205. Persons of ordinary skill in the art, however, will recognize that different angles can be utilized depending on the storage apparatus and slide arrangements. Slides 100 are inserted into the slide storage apparatus 200 so that a bottom surface 102a of a bottom slide 100a is placed on the top surface 216 of the angled base support 210. The remaining slides 100 are stacked on top of the bottom slide 100a at an angle relative to the horizontal 205. Thus, the slides 100 are stacked between the lateral support members 220 and 230 in an angled, non-overlapping manner.

The apparatus 200 can be tilted from the upright position (FIG. 2A), in which the slides are stored at an angle, to a tilted position (FIG. 2B), in which the slides are stored in a generally horizontal manner. Tilting the apparatus 200 in this manner orients the angularly stacked slides 100 in a horizontal position so that they can be selected by the platform fingers 134. In a specific implementation, about 100 slides having a width of about 1" are stacked to a height of about 4.3". An apparatus 200 can be tilted to an angle corresponding to angle 214.

Figure 2B:
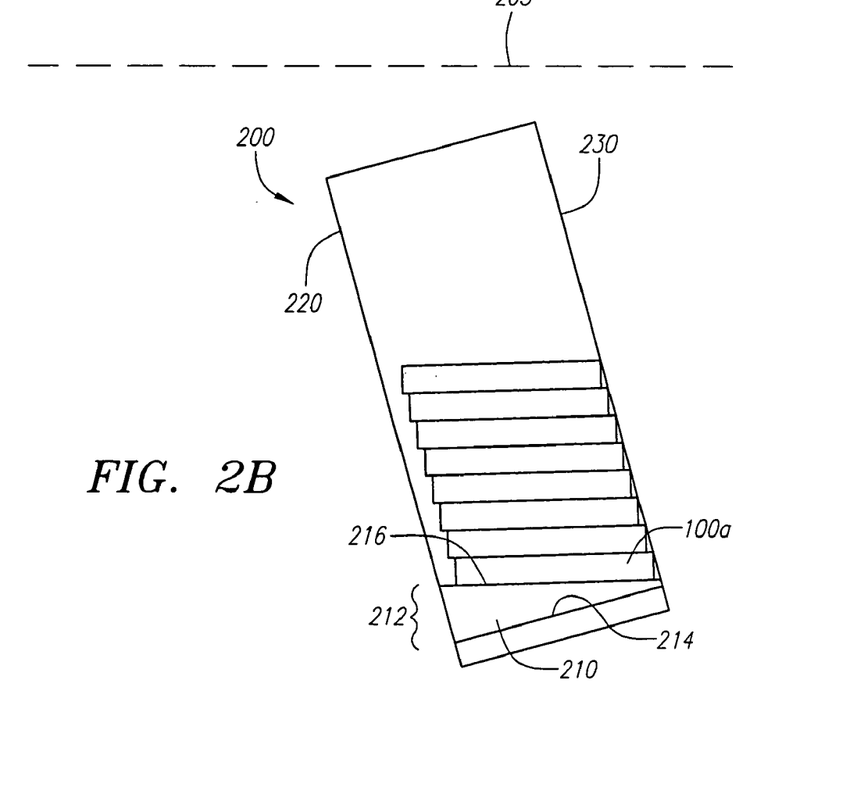

The configurations shown in FIGS. 2A–B have a number of advantages over typical overlapping or aligned slide stacking arrangements. First, the present invention reduces the amount of force required to remove a bottom slide from a stack of slides. For example, with a stack of 80 slides arranged in a conventional, overlapping manner, it was observed that a force of about 6.4 ounces was needed to push the bottom slide out from underneath the remaining 79 stacked slides. With the arrangement shown in FIG. 2A, however, it was observed that the bottom slide 100a was pushed at a downward angle through the slot and out from underneath the remaining slides with about 2.5 ounces. The next slide, slide 100b, would then fall down to the exit position previously occupied by slide 100a.

When tilting the stack of slides, as shown in FIG. 2B, and pushing the slides in a horizontal manner, it was observed that slightly more than 2.5 ounces of force, but less force than 6.4 ounces, was required to push out the slide. The reduction in the required force in the arrangement of FIG. 2B is due, in part, to the bottom edges of one or more slides being partially supported by a lateral support member. For example, the edges 106 rest on the first lateral support member 220 in the tilted configuration. As a result, less weight is applied to the bottom slide 100a. Further, since the arrangements of FIGS. 2A–B provide slides that are offset from each other, a processing system 120 can pick or select a single slide from angularly stacked slides in a more reliable manner compared to conventional overlapping arrangements. More specifically, a lip 134 of a finger 124 can more fully engage a side of the bottom slide since the side is now separated from the side of the next slide above.

Figure 3:
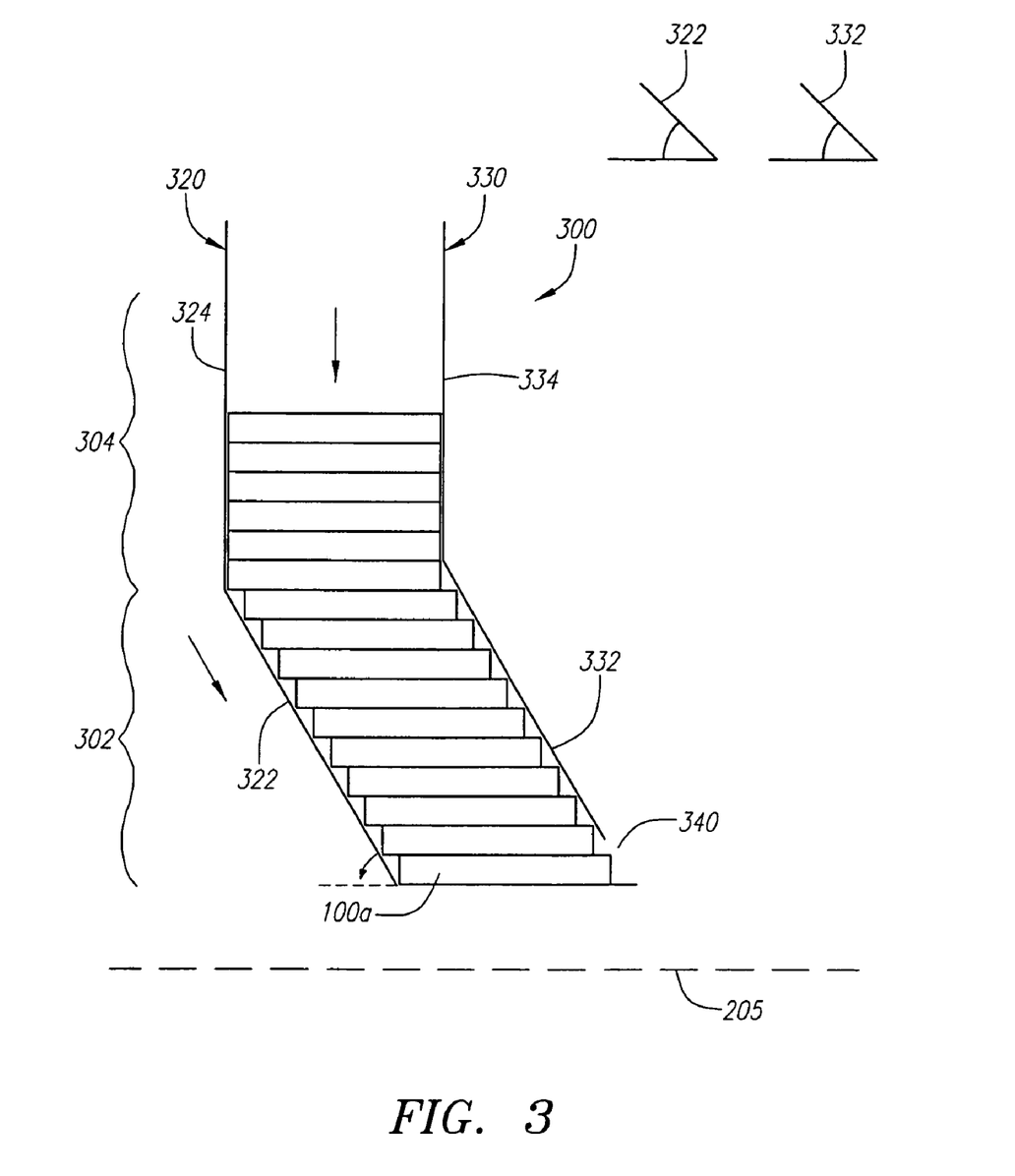
FIG. 3 is a side view of an alternative embodiment of the present invention that includes one or more stacked slides on top of offset slides that are stacked on a horizontal base member.

Referring to FIG. 3, in an alternative embodiment, the apparatus 300 includes angularly stacked slides and slides that are stacked on top of each other in an overlapping or aligned manner. In the depicted embodiment, the apparatus 300 includes a lower section 302 and an upper section 304. The lateral support members 320 and 330 include upper sections 324 and 334, which are generally perpendicular to the horizontal 205, and angled lower sections 322 and 332, similar to FIG. 2B. One or more additional slides 100 in the upper section 304 are stacked on top of the angularly stacked slides 100 in the lower section 302. The additional top slides may be stacked in an overlapping manner, as is known in the art. However, as slides are removed through the slot 340, the higher slides drop down and transition from the straight upper section 304 to the angled lower section 302. Thus, the previously aligned slides shift into a non-overlapping or angular arrangement, as previously discussed in connection with FIGS. 2A–B. Persons of ordinary skill in the art will recognize that various dimensions may be suitable for different apparatus configurations. For example, the height or length of the upper section 324, height of the upper section 334, height of the lower section 322, height of the lower section 332, angle of the lower section 322, and angle of the lower section 332 can be selected based on, for example, the apparatus dimensions, desired offset or fanning effect and number of stored slides.

The apparatus 100 can store only a few slides or as many as 100 slides or more if necessary. Thus, the arrangement shown in FIGS. 2A–B and FIG. 3 provide the ability to store various numbers of slides, while still retaining the angular configuration to allow individual slides to be picked by fingers of a transport platform in a reliable manner.

FIGS. 4A–E illustrate various additional alternative embodiments according to the present invention. These alternative embodiments can include regularly stacked slides and slides that are stacked in a non-overlapping or angular arrangement according to the present invention.

Figure 4A:
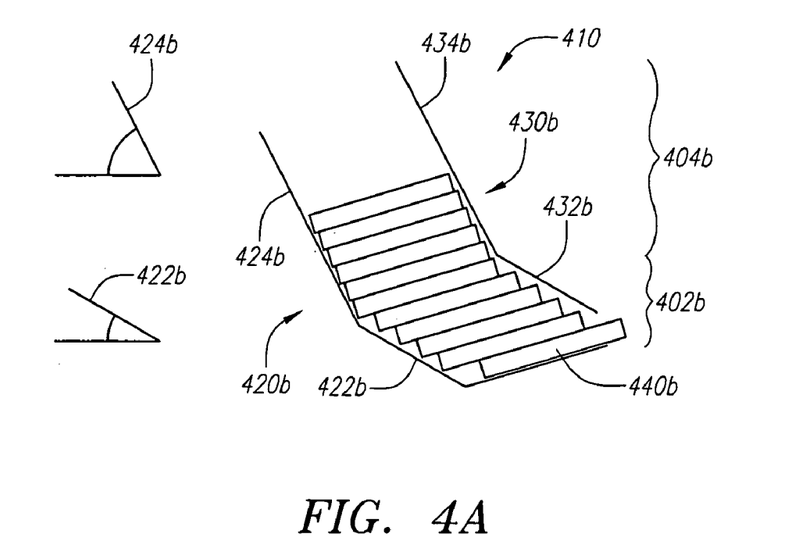
FIGS. 4A–E illustrate alternative embodiments that provide angled, offset and fanning slide arrangements.

Referring to FIG. 4A, in another alternative embodiment, the apparatus 410 includes a lower section 402b and an upper section 404b with lateral support members 420b and 430b. The first lateral support member 420b includes a first angled section 422b and a second angled section 424b. The second lateral support member 430b also includes a first angled section 432b and a second angled section 434b.

Figure 4B:
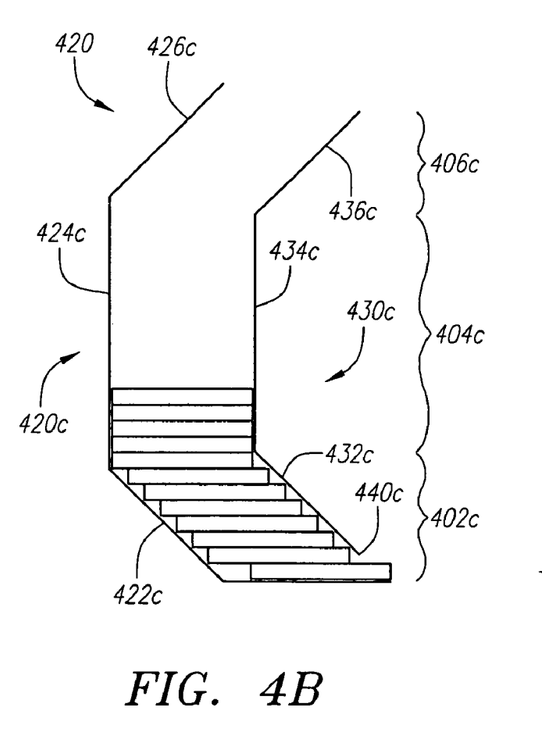
Figure 4C:
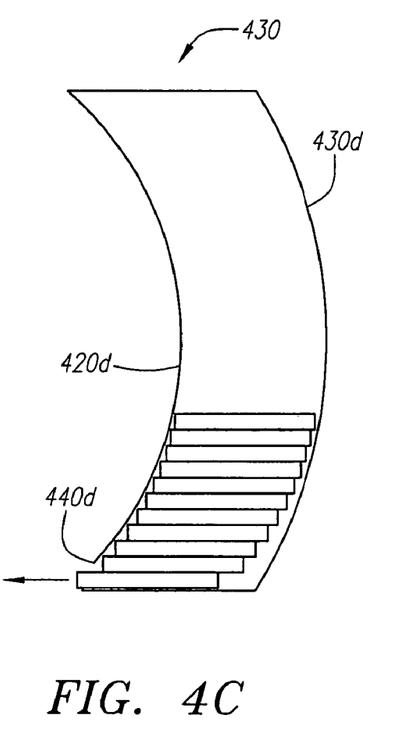

Referring to FIG. 4B, in an additional alternative embodiment, the apparatus 420 includes, a lower section 402c, a middle section 404c, and an upper section 406c with first and second lateral support members 420c and 430c. The first and second lateral support members 420c and 430c each includes a lower or first angled section 422c and 432c, a middle straight section 424c and 434c, and a second angled section 426c and 436c. The second angled sections 426c and 436c extend in a different direction than the lower, first angled sections 422c and 432c. Referring to FIG. 4C, in yet a further alternative embodiment, apparatus 430 includes first and second lateral support members 420d and 430d having an arcuate shape. The arcuate shape facilitates angular stacking and horizontal and vertical fanning arrangements. Thus, the slides at the bottom of the stack are arranged in an angular, non-overlapping manner.

Figure 4D:
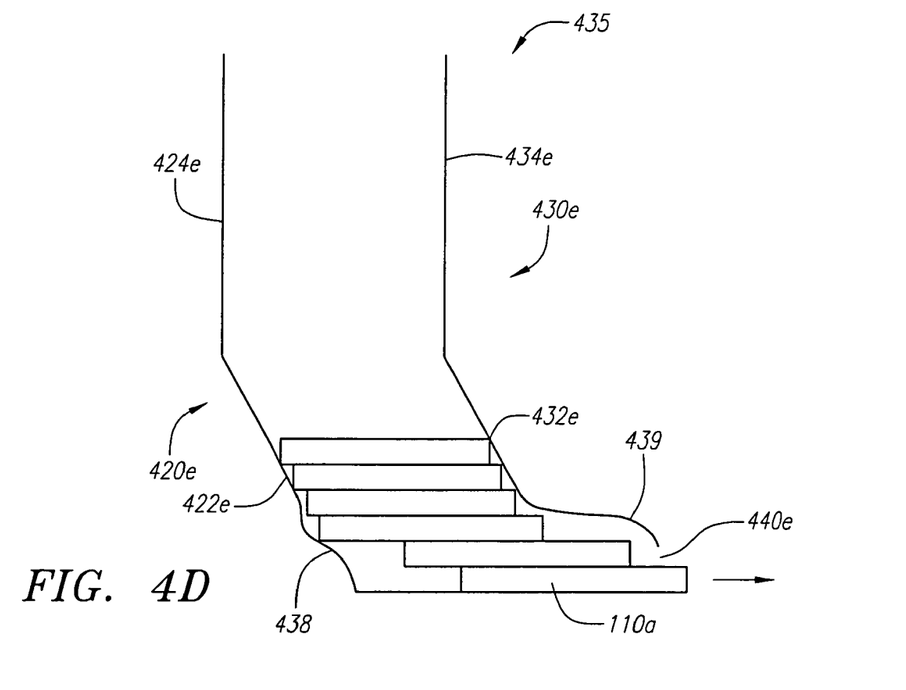
Figure 4E:
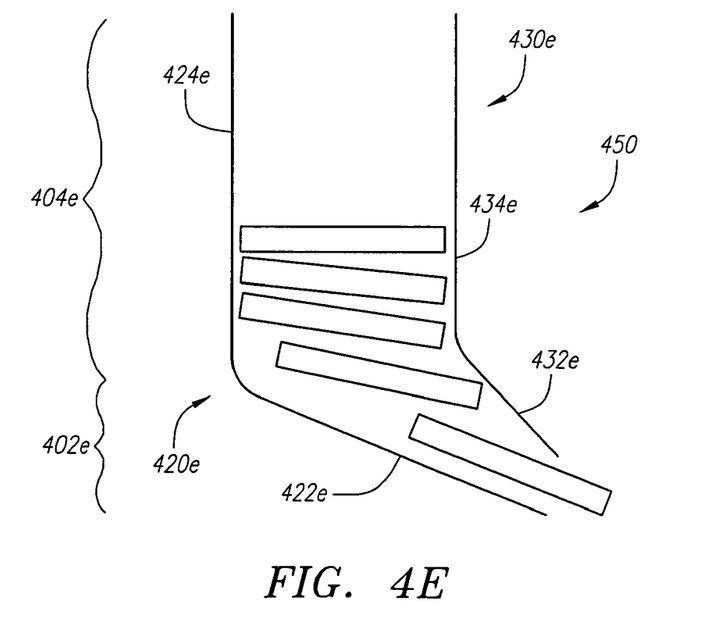

Referring to FIG. 4D, in a further alternative embodiment, the apparatus 440 includes lateral support members 420e and 430e with flared lower sections 438 and 439 to facilitate placement of the bottom slide 110a in the exit slot 440e. FIG. 4E illustrates yet an additional alternative embodiment. The apparatus 450 includes, a lower section 402e and an upper section 404e with first and second lateral support members 420e and 430e. The first and second lateral support members 420e and 430e each includes a lower or first angled section 422e and 432e and an upper, second, vertical or angled section 424e and 434e. With these alternative embodiments, persons of ordinary skill in the art will recognize that the angles of the angled sections may be adjusted to accommodate various apparatus and slide configurations and fanning effects.

With these configurations, slides 100 can be stacked in both angular arrangements in an overlapping manner. However, as the slides drop and transition from a straight or overlapping stacking section to an angled section, they shift into a non-overlapping or angular arrangement, as previously discussed in connection with FIGS. 2A–B and 3. Further, one or more slides can be supported by the first and second lateral support members to remove the weight from being applied to the lower slides, particularly the bottom slide in the stack.

Figures 5A, 5B:
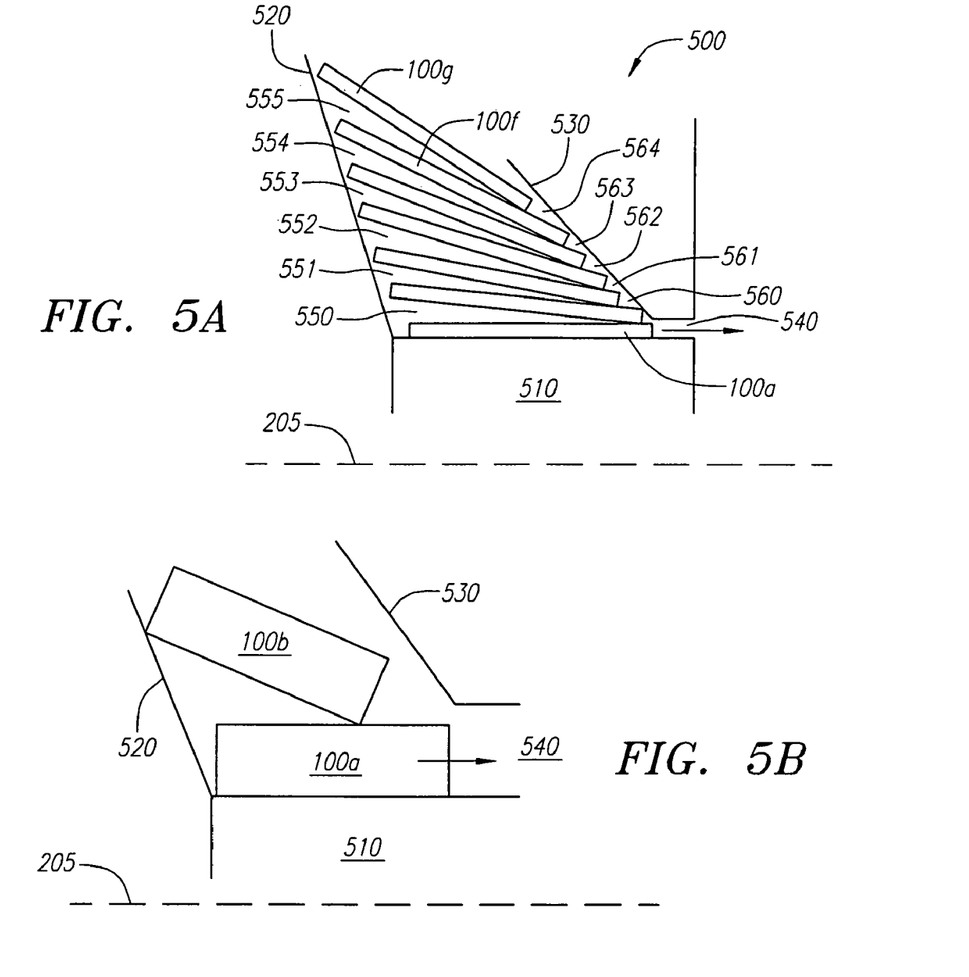
FIGS. 5A–B are side views of a further alternative embodiment showing a fanning arrangement of slides.

FIG. 5A shows one embodiment of slides being arranged in a fanning arrangement. FIG. 5B shows the positioning of the bottom two slides 100a and 100b in such a fanning arrangement. In this apparatus 500, the base member 510 is generally horizontal, and the first and second lateral support members 520 and 530 are angled relative to the horizontal 205. A slot or gap 540 is defined between a bottom surface of the second lateral support member 530 and the base member 510. The slot 540 is large enough so that the bottom slide 100a can be dispensed through the slot 540 when engaged by a lip of a platform finger. In the depicted embodiment, the slides that are higher in the fanning arrangement, such as slides 100*f–g*, are at a steeper angle relative to the horizontal 205 compared to slides that are lower in the fanning arrangement, such as slides 100*a–b*. The angles of the first and second lateral support members 520 and 530 can be adjusted to provide various angular and fanning arrangements with different angular configurations.

The fanning arrangement results in a series of generally angled gaps 550–555. The arrangement may also result in a series of generally triangular gaps 560–564. As a result, the weight that would otherwise be applied to the lower slides, particularly the bottom slide 100*a*, is assumed by the first lateral support member 520. For example, the left bottom edges of slides 100*b–g* rest on the first lateral support member 520. This relationship is illustrated in further detail in FIG. 5B.

Figure 6A:
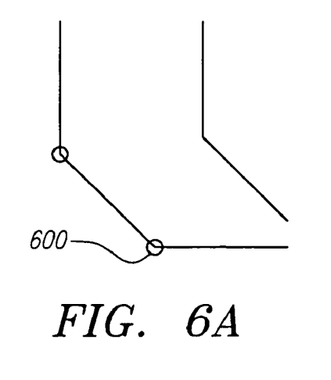
FIGS. 6A–B illustrate various arrangements of friction reducing elements in arrangements according to the present invention.
Figure 6B:
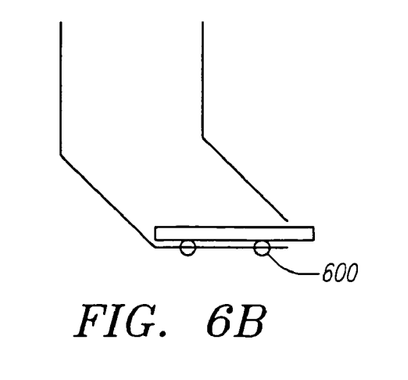

Referring to FIGS. 6A–B, if necessary, friction reducing elements 600 can be incorporated into various apparatus configurations to facilitate downward shifts of a slide and dispensing of a slide out of the apparatus. Exemplary friction reducing elements include, but are not limited to, one or more rollers, bearings, and sliding membranes. Friction reducing elements may be is inserted, for example, between the upper and lower lateral support sections and in the bottom of the lower lateral support section. As a result, the slide traverses down through the support sections more easily with the aid of a friction reducing element.

Figure 7:
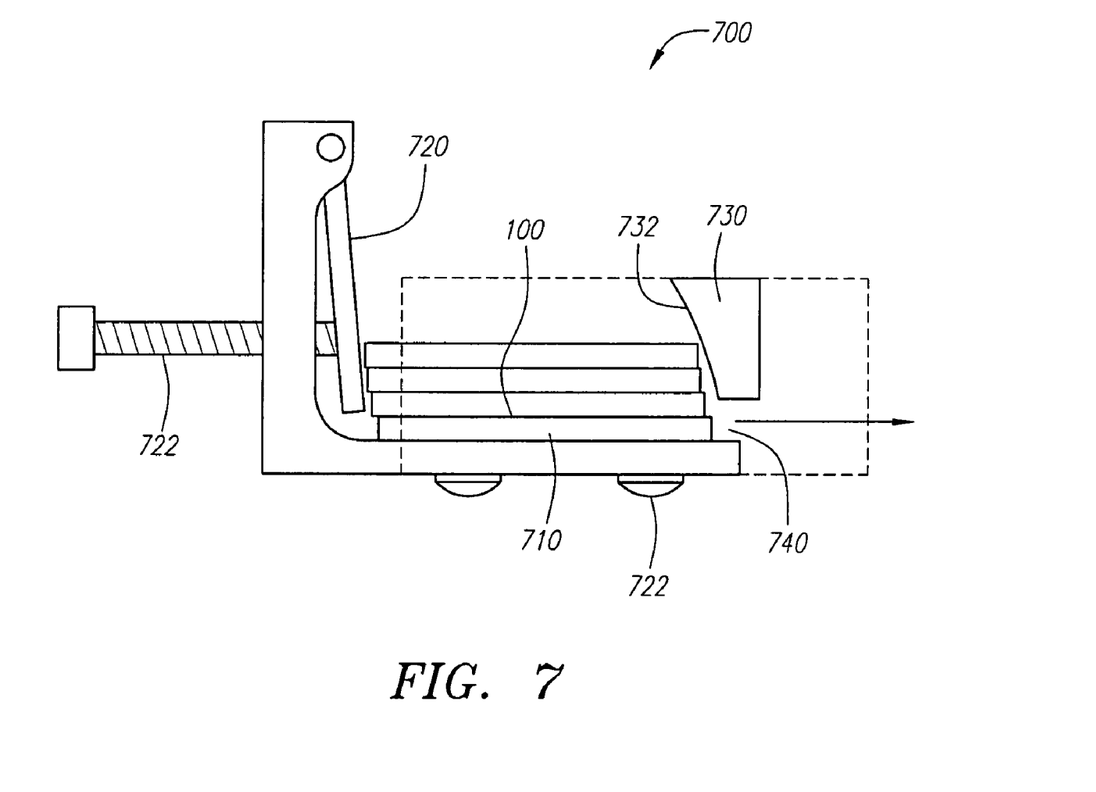
FIG. 7 is a partial side view of an apparatus for storing slides in an angular arrangement according to the present invention.

FIG. 7 illustrates a slide storage apparatus 700 according to the present invention. The apparatus 700 stores slides in an angular or fanning arrangement so that the slides are not stacked in a "slide on slide" configuration. Although the depicted embodiment illustrates only a few slides, persons of ordinary skill in the art will appreciate that the apparatus can be appropriately expanded to store various other numbers of slides for example, 10 to 100 slides, utilizing only angular stacking or a combination of angular and straight stacking.

In this particular implementation, FIG. 7 partially illustrates the apparatus 700 as a cartridge that is inserted into a slide bank (not shown). The edges of the bottom slide are supported by a base member 710. A retaining spring (not shown), which prevents slides from falling through the slot 740, is displaced when inserted in the slide bank, thereby opening the slot 740 below the second lateral support member 730. The retaining spring is useful, for example, when the slides are in storage or when the cartridge is being transported.

In the depicted embodiment, the first lateral support member 720 is a plate that is rotatably adjustable about a hinge or other suitable connector. When the member 720 contacts sides of the slides, side and bottom adjustment screws 722 can be adjusted to move the member 720, as necessary, to adjust the angle and position of the member 720. In the depicted embodiment, the second support member 730 has an angled face 732 with a fixed angle. In an alternative embodiment, the second support member 730 may also be adjustable. Further, persons of ordinary skill in the art, however, will recognize that the lateral support members 720 and 730 can both be fixed, both be adjustable, or that one of the support members can be adjustable, as shown in FIG. 7. As a result of the angles formed by the first and second support members 720 and 730, the slides are not stacked directly on top of each other and instead, are arranged on top of each other in an offset, angled or staggered configuration. Thus, the bottom slide can be positioned so that an adjacent top slide is not stacked directly on top of the bottom slide so that when the bottom slide moves along the base 710 and underneath the second support member 730, a slide transport system can easily grasp the slide at the bottom of the stack, without inadvertently retrieving two slides at once.

In use, the lip 134 of the fingers 124 of the platform 122 engage the bottom edge of the bottom slides and push the slide forward through the slot. As a result, the slide 100*a* falls down onto the coated slide surfaces. The next slide 100*b* above the dispensed slide 100*a* then falls down into the exit or slot position, and the other slides also fall down further as more slides are dispensed. With this configuration, the lip of the finger engages a single slide and is able to locate the edge of the slide as a result of the angled or fanning arrangement.

Figure 8:
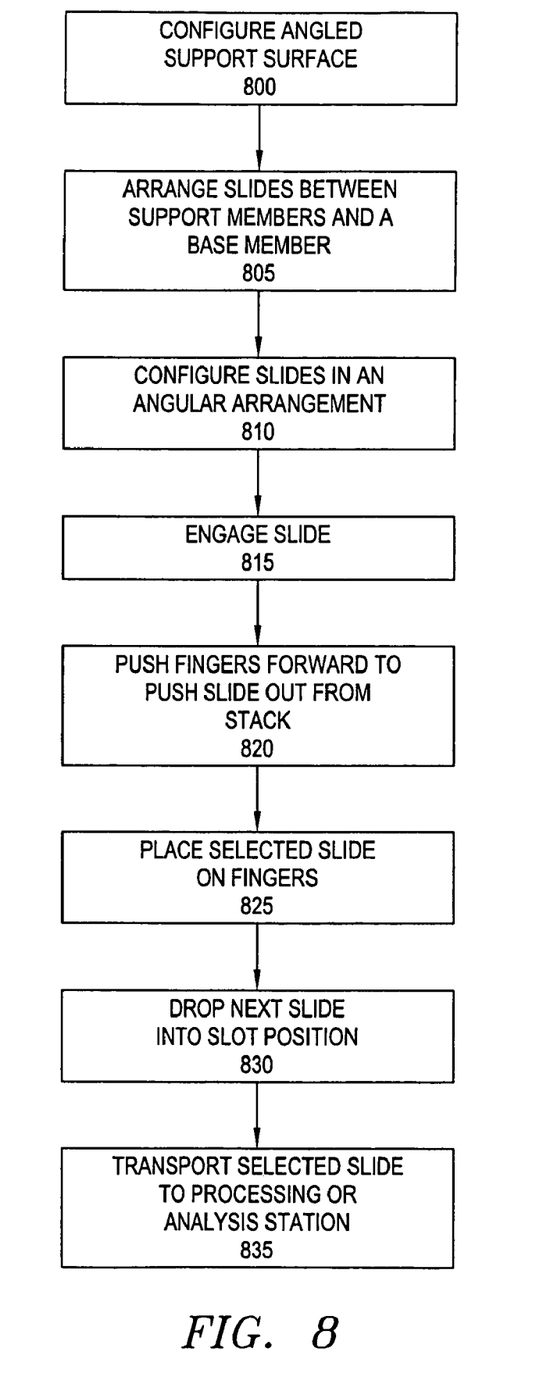
FIG. 8 is a flow diagram illustrating a method of angularly stacking slides according to the present invention.

Having described various embodiments of an apparatus according to the present invention and the manner in which the apparatus is utilized, following is a description of a method of storing a plurality of slides in a slide storage apparatus according to the present invention and dispensing slides from the apparatus. Referring to FIG. 8, initially, at stage 800, the apparatus is configured with an angled support surface. The angled support surface can be an angled base member (e.g., FIGS. 2A–B) or an angled lateral support member (e.g., FIGS. 4E, 5A–B). In the case of angled lateral support members, the angles can be fixed or adjustable depending on the desired angled or fanning arrangement. In stage 805, the plurality of slides are arranged between the lateral support members and on the base member. As a result, in step 810 the slides are angularly arranged in, for example, a fanning arrangement. In step 815, a lip of a platform finger engages a bottom slide in the stack of slides. In step 820, the fingers are pushed forward, thereby pushing the bottom slide out from underneath the stack of slides. In step 825, the selected slide is placed on the fingers. In step 830, the next slide above the dispersed slide drops down into the exit or slot position and is ready to be removed from the cartridge. In step 835, the selected slide is carried on the fingers and transported to a processing or analysis station.

The apparatus and method of the present invention is advantageous compared to typical "slide-on-slide" or aligned stacking. For example, the angled or fanning arrangement reduces the force or weight upon each slide, particularly the bottom slide to be dispensed from the container. As a result, the present invention allows slides to be dispersed from a cartridge with less force. The angled/fanning arrangement also permits the finger to apply maximum engagement while picking and transporting individual slides more accurately compared to conventional systems. For example, since the next slide is offset or displaced from an adjacent slide, a thicker finger or engagement surface can be utilized to more accurately engage an individual slide. The angled/fanning arrangement also distributes the weight of a stack of slides away from the bottom or lower slides. Thus, present invention improves slide selection while also reducing damage to slides. These improvements are particularly beneficial with larger stacks of slides since weight and friction increase with greater numbers of slides.

Further, a processing system is more likely to retrieve a single slide that is angularly stacked or stacked in a fanning arrangement since the processing system is not required to select a slide that is part of a stack of other evenly stacked slides. In other words, the slides are no longer aligned and stacked on top of each other but are, instead, horizontally and/or vertically staggered as a result of angular stacking so that the processing system is more likely to retrieve an individual slide. Thus, the present invention can be used with processing systems with varying slide selection tolerances and accuracy and improves slide processing.

Having described the apparatus for removably retaining or securing a slide within a cassette according to the present invention, persons of ordinary skill in the art will recognize that the above apparatus can be modified in various ways to perform the same retaining functions. For example, the dimensions and angles can be adjusted to provide different angles or fanning arrangements and to accommodate storing different members of slides. As a further example, the base, the first lateral support member, the second lateral support member, or a combination thereof, can include an angled surface to provide an angled, offset or fanning arrangement. Moreover, a cartridge according to the present invention may include only angled sections or a combination of straight and arcuate sections to provide the desired stacking effect. Accordingly, persons of ordinary skill in the art will appreciate that the invention is not limited to the particular exemplary embodiments described, but rather, the invention encompasses various other flexible and molded support members within a slide cassette.

Although references have been made in the foregoing description to various embodiments, persons of ordinary skill in the art of slide cassette and storage receptacles and related slide processing and analysis systems will recognize that insubstantial modifications, alterations, and substitutions can be made to the described embodiments without departing from the invention as claimed in the accompanying claims.

What is claimed is:

1. An apparatus for storing a plurality of slides in an angular arrangement, the apparatus comprising:
   a base member for providing vertical support to the plurality of slides, a top surface of the base member being substantially parallel to a horizontal;
   a first support member arranged at a first angle relative to the horizontal; and
   a second support member arranged at a second angle different from the first angle relative to the horizontal,
   the plurality of slides being angularly stacked in a fanning arrangement relative to the horizontal on the base member and between the first and second support members so that at least the two bottom slides of the plurality of slides are offset and the edges of adjacent slides do not overlap each other.

2. The apparatus of claim 1, the first angle being different than the second angle.

3. The apparatus of claim 1, the first support member being fixed at the first angle.

4. The apparatus of claim 1, the second support member being fixed at the second angle.

5. The apparatus of claim 1, the first support member being adjustable.

6. The apparatus of claim 1, the second support member being adjustable.

7. The apparatus of claim 1, a bottom slide of the plurality of slides being dispensed through a slot defined between one of the support members and the base member.

8. The apparatus of claim 7, wherein only the bottom slide of the plurality of slides is dispensed through the slot.

9. The apparatus of claim 1, the plurality of angularly stacked slides having a fanning arrangement.

10. The apparatus of claim 1, further comprising a friction reducing member that contacts one or more slides.

11. The apparatus of claim 1, wherein the first angle is an angle of a surface of the first support member that contacts the slides, and the first angle is greater than 90 degrees relative to the horizontal.

12. The apparatus of claim 1, wherein the second angle is an angle of a surface of the second support member that contacts the slides, and the second angle is less than 90 degrees relative to the horizontal.

13. The apparatus of claim 1, wherein a gap exists between each slide in the angularly stacked plurality of slides.

14. The apparatus of claim 1, wherein no slide lies flatly upon another slide in the angularly stacked plurality of slides.

15. The apparatus of claim 1, wherein a higher slide in the plurality of slides is arranged at an angle that is steeper than the angle at which a lower slide in the plurality of slides is arranged.

16. The apparatus of claim 1, wherein the fanning arrangement results in a series of angled gaps defined by one of the support members and adjacent slides.

17. The apparatus of claim 1, wherein the fanning arrangement results in a series of generally triangular gaps defined by one of the support members and adjacent slides.

18. The apparatus of claim 1, wherein the first support member extends upwardly from the base, and the second support member extends downwardly towards the base, wherein the slot is defined between the base and the bottom of the second support member.

19. The apparatus of claim 18, wherein the second support member supports each slide of the plurality of slides except the bottom slide, wherein the bottom slide is dispensed through the slot.

20. The apparatus of claim 1, wherein each slide is stacked at a different angle.

21. The apparatus of claim 1, wherein the first and second angles are angles other than 90 degrees relative to the horizontal.

22. The apparatus of claim 21, wherein the first angle is greater than 90 degrees and the second angle is less than 90 degrees.

* * * * *